(12) United States Patent
Dufresne et al.

(10) Patent No.: US 6,537,459 B1
(45) Date of Patent: Mar. 25, 2003

(54) METHOD AND APPARATUS FOR ETCHING-MANUFACTURE OF CYLINDRICAL ELEMENTS

(75) Inventors: Michael J. Dufresne, Inver Grove Heights, MN (US); LeRoy J. Lundblad, St. Paul, MN (US)

(73) Assignee: BMC Industries, Inc., Minneapolis, MN (US)

( * ) Notice: Subject to any disclaimer, the term of this patent is extended or adjusted under 35 U.S.C. 154(b) by 0 days.

(21) Appl. No.: 09/553,069

(22) Filed: Apr. 20, 2000

Related U.S. Application Data

(62) Division of application No. 09/083,703, filed on May 22, 1998, now Pat. No. 6,086,773.

(51) Int. Cl.[7] .................................................. A61F 3/00
(52) U.S. Cl. .............................. 216/8; 216/41; 216/52; 216/92; 216/100
(58) Field of Search .............................. 216/8, 41, 52, 216/56, 92, 100

(56) References Cited

U.S. PATENT DOCUMENTS

| | | | |
|---|---|---|---|
| 4,233,108 A | * 11/1980 | Tamura et al. | 156/345.2 |
| 4,600,470 A | * 7/1986 | Maynard et al. | 216/54 |
| 4,799,993 A | * 1/1989 | Hagan | 137/888 |
| 5,421,955 A | 6/1995 | Lau et al. | 216/48 |
| 5,437,288 A | 8/1995 | Schwartz et al. | 128/772 |
| 5,603,721 A | 2/1997 | Lau et al. | 606/195 |
| 5,649,952 A | 7/1997 | Lam | 606/198 |
| 5,741,429 A | 4/1998 | Donadio, III et al. | 216/8 |
| 5,855,802 A | 1/1999 | Acciai et al. | 216/8 |
| 5,902,475 A | * 5/1999 | Trozera et al. | 205/151 |
| 6,019,784 A | * 2/2000 | Hines | 128/898 |

* cited by examiner

Primary Examiner—Allan Olsen
(74) Attorney, Agent, or Firm—Oppenheimer Wolff & Donnelly, LLP

(57) ABSTRACT

A process is described for the manufacture of flexible tubular elements, particularly stents for the medical field, the process comprising the steps of:

a) providing a hollow metal tube (or metal coated tube) with an open pattern of a chemical-etch-resistant coating layer;

b) supporting the hollow metal tube with a coating thereon onto a chemical etch resistant support element;

c) contacting the open pattern with a solution capable of etching the metal of the hollow metal tube so that said metal is etched away from physically exposed surfaces of the metal tube and openings in the metal tube corresponding to the open pattern of the coating layer are created in the metal tube element without etching the chemical etch resistant support element; and d) removing the metal tube from the chemical etch resistant support element.

10 Claims, 4 Drawing Sheets

METHOD AND APPARATUS FOR ETCHING-MANUFACTURE OF CYLINDRICAL ELEMENTS

This application is a divisional of U.S. application Ser. No. 09/083,703, filed May 22, 1998, now U.S. Pat. No. 6,086,773 which application is incorporated herein by reference.

BACKGROUND OF THE INVENTION

Field of the Invention

The present invention relates to an etched tubular device, particularly cylindrical, biocompatible medical devices for insertion into a body during medical procedures and to a method for manufacturing these devices. More particularly, the invention relates to flexible tubular devices for use as stents, catheters (including, for example, guide catheters and balloon catheters, guidewires, catheter sheaths, microcircuitry containing catheters, catheter introducers and drug infusion catheters/guidewires) and methods for making these devices.

Catheters and Guidewires

Catheters are relatively thin and flexible tubes used in the medical field for numerous applications. Catheters are made by any number of different methods and designs. However, in most catheter designs it is desirable to obtain a maximum torsional rigidity while retaining a satisfactory longitudinal flexibility and stiffness without kinking. These features allow the catheter to be manipulated so that the catheter can be guided through small body vessels and cavities. These features will also prevent any kiking from occurring, and provide the catheter with sufficient stiffness to prevent the catheter from wrinkling or folding back on itself during this process. The specific nature of these characteristics vary depending on the specific application for which the catheter is being used. Another consideration is that a relatively small outside diameter must be maintained while providing a lumen or an inside diameter as large as possible.

Guidewires require the same general type of physical characteristics. However, with guidewires it is important to minimize the outside diameter of the guidewire so that they will readily fit inside of the lumen of the catheter.

Catheters and guidewires are used both as diagnostic tools and therapeutic tools in the treatment of diseases. One such diagnostic procedure is cardiac catheterization which is a widely performed procedure, being used for assessment of coronary artery disease. Other uses are neurologic uses, radiologic uses, electrophysiologic uses, peripheral vascular uses, etc. Example of therapeutic uses are balloon catheterization in dilation procedures to treat coronary disease and retroperfusion delivery of drugs at targeted sites within the human body. Dilation procedures rely upon the use of a catheter for injection of contrast and delivery of guidewires and dilation catheters to the coronary artery or other arteries. An example of the use of guidewires is for Percutaneous Transluminal Coronary Angioplasty (PTCA) balloons and for guiding diagnostic catheters through the arteries and to body organs. Retroperfusion drug delivery requires the use of the catheter to guide a tube carrying the drug to be delivered, and in some cases to have the catheter determine part of the rate of perfusion by the size, number and distribution of openings in the catheter through which the drug will pass.

The catheters and guidewires used in these and other procedures must have excellent torque characteristics, and must have the requisite flexibility. In addition, it is important that catheters and guidewires provide sufficient longitudinal support for "pushing" of items through the arteries and other vessels such as when feeding the balloon portion of an angioplasty catheter through the arteries. Unless there is sufficient stiffness, the catheter or guidewire will wrinkle or fold back on itself Typically, in the case of a catheter, the larger the ratio of inside to outside diameter, the better, even while striving for minimum outside diameters for the catheters. Smaller catheter and guidewire outside diameter sizes result in less chance of arterial damage.

Catheters and guidewires must have sufficient torque to reduce buckling when being manipulated. Additionally, flexibility is important so that the catheter or guidewire can be manipulated into the varying arterial branches encountered by the catheter. The guidewire must resist being inadvertently kinked, as this can result in loss of torque control.

Prior art catheters are typically made of flexible materials which are reinforced such that the resulting composite catheter approximates the desired characteristics. In alternative approaches, guidewires are used in conjunction with catheters to assist in manipulating and moving the catheters through the arterial system in the body.

Stents are small, expandable tubes, usually used for insertion into a blocked vessel (vein or artery or duct) or other bodily part. Their physical characteristics must often be the same as those for catheters, except for the fact that they also must be expandable. This expansiveness is effected, not by elastic expansion under pressure, as is the case with balloons or parachutes in surgical procedures, but by more spring-like, metal memory characteristics in the material. Stents are often formed of a metal tube which is compressed (without exceeding the elastic flexibility or stress of the metal), inserted, and then released to allow the stent to expand to its original size and shape.

U.S. Pat. No. 4,020,829 discloses a spring guidewire for use in catheterization of blood vessels. The guidewire is axially slidable within a thin-walled, flexible plastic catheter. The distal portion of the guidewire is of a relatively short length and is connected to a relatively long, manipulative section capable of transmitting rotational torque along its length. In this invention the catheter tube might be advanced over the guidewire after the guidewire has been properly positioned or the catheter might be advanced together with the guidewire, the guidewire providing a reinforcement for the thin wall of the catheter.

U.S. Pat. No. 4,764,324 discloses a method for making a catheter. A reinforcing member is heated and applied to a thermoplastic catheter body so as to become embedded in the wall of the catheter. The wall of the catheter is then smoothed and sized so as to produce a composite, reinforced catheter.

Current catheters often suffer from either problems of torque, size, flexibility, kinking, and poor support during PTCA in the case of guide catheters. Moreover, catheters cannot be readily made with variable stiffness along the length of the catheter.

Catheter Sheaths and Introducers

Catheter sheaths and introducers are used to provide a conduit for introducing catheters, fluids or other medical devices into blood vessels. A catheter introducer typically comprises a tubular catheter sheath, a hub attached to the proximal end of the sheath having hemostasis valve means to control bleeding and to prevent air embolisms, and a removable hollow dilator that is inserted through the hub, valve means and the lumen of the catheter sheath. Many catheter introducers also contain a feed tube that is connected to the hub to facilitate the introduction of fluids into the blood vessel.

Positioning an introducer into a blood vessel begins by inserting a hollow needle through the skin and into the lumen of the desired blood vessel. A guidewire is then passed through the needle and into the blood vessel. The needle is then removed leaving the guidewire in the vessel. Next, the sheath and dilator are advanced together over the guidewire until the distal ends of the dilator and sheath are positioned within the lumen of the vessel. The guidewire and dilator are then removed, leaving the distal end of the sheath within the vessel. Catheters or other medical devices can then be passed through the introducer and sheath into the desired vessel.

Conventional sheaths are made of plastic and are subject to kinking if bent without internal support. This kinking can occur during the insertion of the device or if the patient moves while the sheath is in the vessel. Unfortunately, this kinking can create sharp edges or irregularities in the sheath that can damage blood vessel linings. This kinking can also make the introduction of devices or fluids more difficult and can cause patient bleeding problems around the sheath tubing. Therefore, there arises a need for a catheter introducer with a catheter sheath that is flexible and resistant to kinking.

Drug Infusion Catheters/Guidewires

Drug infusion catheters/guidewires are devices that act like both catheters and guidewires and are capable of delivering drugs or other fluids to a specific location within a patient's blood vessel such as an occluded blood vessel. The guidewire type devices are typically comprised of a coil spring with a heat-shrunk TEFLON® coating and a core wire that can be inserted and removed from the lumen in the coil spring. The coated coil also contains either side holes or an end hole or a combination thereof in its distal end to enable the drugs or other fluids to be sprayed into the blood vessel.

During use, the coated coil spring and its core wire are advanced together through the patient's circulatory system much like conventional guidewires. Upon reaching the desired location, the core wire is removed creating a small catheter-like device. Drugs or other fluids are pumped through the lumen in the coated coiled spring, out of the holes and into the blood vessel at the desired location.

Because these devices act like guidewires, the outside diameter of the devices, and therefore the lumen, are limited in size. Therefore, a second type of drug infusion catheter/guidewire device utilizes a catheter-like member with side holes and a tapered distal end having an end hole generally equal to the outside diameter of a guidewire. These catheter-type drug infusion catheter/guidewire devices are advanced over a guidewire to the desired location and then drugs are then pumped through and out of the holes in the catheter-like member. These devices can also be used in combination with the guidewire-type drug infusion devices.

As described above, drug infusion catheter/guidewire devices act like both catheters and guidewires. Therefore, these devices must have the same characteristics as catheters and guidewires. These devices must obtain a maximum torsional rigidity while retaining a satisfactory longitudinal flexibility and stiffness without kinking. They must also maintain a small outside diameter while providing a lumen as large as possible.

Stents

Stents are devices that are placed into and/or implanted in the body, and in particular in body structures including vessels, tracts or ducts. For example, stents are commonly used in blood vessels, the urinary tract and in the bile duct, to treat these body structures when they have weakened. With blood vessels, stents are typically implanted therein to treat narrowings or occlusions caused by disease, to reinforce the vessel from collapse or to prevent the vessel from abnormally dilating, as with an aneurysm or the like.

Stents are typically produced at a first smaller diameter for deployment and then expanded to a larger diameter, upon placement into the body vessel, tract, duct or the like. Deployment of stents it typically achieved by mounting the stents on balloon catheters and then once at the requisite position in the body vessel, tract, or duct, expanding the stent to the larger diameter, for permanent placement therein. U.S. Pat. No. 4,856,516 to Hillstead discloses a typical stent and describes a method for its deployment and placement with a balloon catheter.

U.S. Pat. Nos. 5,649,952 and 5,603,721 describes an expandable stent, a method for implanting a stent in a patient and a method for making that type of stent. The stent comprises a cylindrical frame which has patterns of materials removed from the cylindrical mass formed of interconnected elements designed to expand evenly under radial stress. In a preferred structure, a serpentine pattern is formed aligned on a common longitudinal stent axis to form elements that expand evenly under radial stress and maximize the overall radial expansion ratio. Although no methods are claimed in the patent for manufacturing the elements, various methods of manufacture are described such as coating a thin walled tubular element with a material which is resistant to chemical etchant, removing patterns of the resist material to expose portions of the underlying tubular element, and subsequently etching to remove a pattern of the tubular material which will leave the designed pattern in the tubular element so that it has a pattern which provides the desired expandability. It is stated that it is preferred to apply the etchant resistant coating by electrophoretic deposition and to remove the etchant-resistant material by means of a machine-controlled laser.

U.S. Pat. No. 5,437,288 describes an apparatus for use as a catheter guidewire and a method for manufacturing a catheter guidewire. The apparatus for use as a guidewire comprises an elongate, non-coiled wire having a flexible portion located between a distal and a proximal end, the distal end (and distal portion) of the apparatus having spaced grooves cut therein. The claimed method of making the guidewire comprises providing a metal wire, cutting a plurality of axially spaced grooves in the metal wire, and increasing the depth of the grooves toward the distal tip to create a flexible portion. The grooves are suggested to be formed in the wire by any suitable machining method, such as grinding, electrostatic discharge machining (EDM), lasers or the like.

WO 97/42910 relates to a novel apertured flexible tubular member with an encasing for insertion into vessels of the body as part of a medical device. For example, the invention can be used as catheters, including guide catheters and balloon catheters, guidewires, catheter sheaths for use with catheter introducers, or drug infusion catheter/guidewires. These catheters also relate to novel apertured flexible tubular stents which may be coated, for insertion into vessels, tracts or ducts. One embodiment is coated with a low friction material such as a low friction polymer so as to provide for lubricity. Samples of materials that might be used are polyurethane, hydrogels, polyethylene, polytetrafluoroethylene (PTFE) and, in particular, one such material which might be used is TEFLON®.

In some embodiments, such as catheters or sheaths, the inside of the flexible tubular member is also preferably coated with a low friction material such as hydrogel and/or with an anticoagulant such as heparin. Another embodiment uses slots of a predetermined configuration cut into a single, hollow, thin-walled metal tube at predetermined spacings, depth and pattern so as to provide the tube with a desired flexibility. The tube is then encased in a suitable low-friction material as noted above or some other suitable coating material. The method of forming the tubular member includes:

a) providing a tubular element including an outer surface;
    b) providing a light source (including columnated light);
    c) creating a pattern on the tubular element by:
        1. applying a photoresistive material to at least a portion of the outer surface of said tubular element,
        2. providing a mask intermediate the tubular element and the light source, at least a portion of the mask including a predetermined pattern formed of predetermined locations translucent to light from the light source,
        3. activating the light source to expose a first area of the photoresistive material on the outer surface of the tubular element,
        4. moving the tubular element such that at least a second area on the outer surface of said tubular element is substantially aligned with said at least a portion of the mask including predetermined locations translucent to light from the light source,
        5. activating the light source to expose the second area of the photoresistive material on the outer surface of the tubular element, and
        6. developing the photoresistive material on the tubular element, to create first portions and second portions of the photoresistive material, the first portions and the second portions corresponding to their respective exposure from the light source (including columnated light); and
    d) removing segments of the tubular element corresponding to the first portions of the photoresistive material.

The mask is shown to include typical stencil-type masks, ink patterns (e.g., applied by a laser printer), and film masks, and either negative-acting or positive-acting resists can be used. Chemical etching of the tube is shown.

SUMMARY OF THE INVENTION

The present invention describes a method for providing a flexible cylindrical element, such as a medical stent, comprising the steps of providing a cylindrical body (e.g., a hollow cylindrical body), coating the cylindrical body with a photosensitive resist material (either positive or negative acting), exposing the photosensitive resist material to focused or coherent radiation to which the photoresist composition is sensitive, developing the exposed photosensitive resist material to a fluid developing environment which will selectively remove areas of the photoresist which are more soluble in the fluid developing environment, and then chemically etching exposed surfaces of the cylindrical element which has been exposed by the development of the photoresist coating. The residual photoresist material may be stripped, the patterned cylindrical element cleaned, inspected, packaged and sent to the end user.

DETAILED DESCRIPTION OF THE INVENTION

Figure 1:
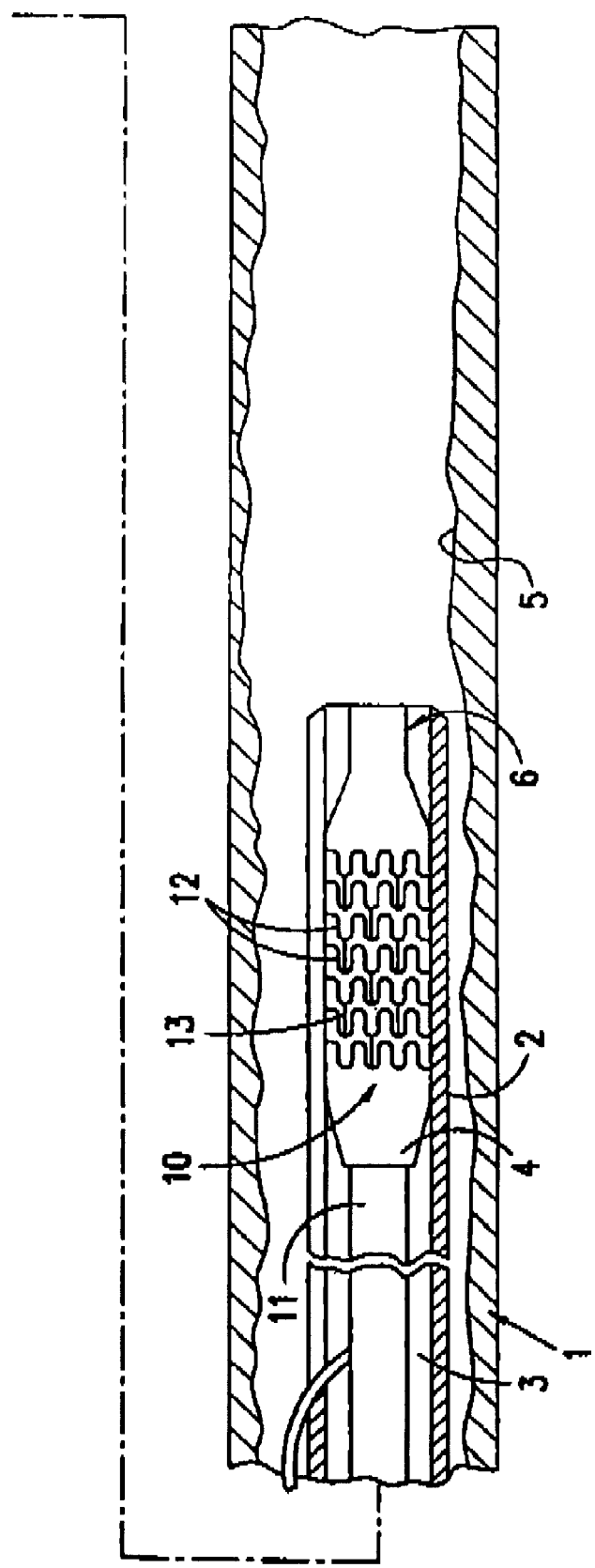
FIG. 1 shows a side view of a typical stent within a catheter within a vein.

As compared to prior art processes, the present invention process is believed to provide some specific technical advantages. For example, direct machining grooving of patterns is complex and less exact than the combined photolithographic imaging and etching process of the present invention. Even when direct laser etching of a surface is to be done with a laser (as suggested in U.S. Pat. No. 5,437,288), the laser energy has to be sufficiently high to etch through the metal. This creates a potential for etching of the inside opposed surface of the tubular element and localized redeposition of ablated metal material within or on the cylindrical element. Removal the etchant-resistant material by means of a machine-controlled laser as suggested in U.S. Pat. Nos. 5,649,952 and 5,603,721 requires actual etching of the resist coating with a laser and subsequent chemical etching of the exposed portions of the underlying cylinder provides similar problems with redeposition of the ablated material. Because heat is generated in the ablative removal of the photoresist coating or explosive ablation of material may occur from rapid volatilization of the coating, and because the underlying metal can conduct heat laterally, there are many control considerations which must be made in such a laser ablation step to effect high resolution and smooth patterns in the resist.

A process according to the invention for the manufacture of hollow tubular metal elements, such as flexible stents, comprises the steps of:

a) providing a hollow metal tube with an open pattern of a chemical-etch-resistant coating layer;
    b) supporting the hollow metal tube with a coating thereon onto a chemical etch resistant support element;
    c) contacting the open pattern with a solution capable of etching the metal of the hollow metal tube so that the metal is etched away from physically exposed surfaces of the metal tube and openings in the metal tube corresponding to the open pattern of the coating layer are created in the metal tube element; and
    d) removing the metal tube from the chemical etch resistant support element.

Contacting of the open pattern is preferably effected by having the metal tube both rotate and revolve, and by having spray which repeatedly alters its angle of spray towards said metal tube. The spray may, for example be provided by banks of nozzles within a spray chamber, and the nozzles or banks of nozzles may shift their positions to change the angle at which the spray is directed towards the exposed metal surface during the etch process. Preferably more than one metal tube is supported within a movable support, and said movable support is passed through an area where chemical etch solution is applied by spraying. The movable support may be a tray carrying the hollow tube elements with the pattern of resist already developed on their surfaces or a bank of supported hollow tube elements, with the supports not covering the surface of the openings in the resist pattern.

The process preferably uses etch solution capable of etching the metal of the metal of the metal tube which are heated above 40° C. Preferred solutions comprise ferric chloride solution, particularly those with a Baume' above 47.5°. The supported cylindrical element (the hollow metal tube) preferably both rotates on a longitudinal axis and is revolved with at least some movement in a direction perpendicular to said longitudinal axis, while the etchant solution capable of etching the metal of the metal tubular element is sprayed onto said at a temperature between 40 and 150° F. Preferably the etchant comprises a ferric chloride solution (with HCl) with a Baume' between 48 and 55 degrees and preferably between 48.5 and 54 degrees at a temperature above 100° F. and between 110 and 140° F.

A laser or focused radiation initiated photoresist imaging process with chemical etching or development of the resist pattern is very controllable and sensitive. Few special treatment, manual or intermediate finishing steps are required to provide the product in a highly automated system. Photoresist development is gentle and non-destructive to the underlying cylindrical surface and collateral damage to the interior backside (inside) of the cylindrical element can be readily avoided. However, even the columnated radiation exposed process of WO 97/42910 is general in description of the process and fails to consider the engineering and physics of the process, and merely discloses a literal use of conventional photolithographic imaging and resist development in a cylindrical exposure method, which occurs on drum supports in photoimaging technology in many different fields. The description of chemical etching also fails to provide any specific advances over standard etch procedures used on flat surfaces and three-dimensional surfaces.

Amongst the steps used in the practice of the present invention (without every step being required in combination with all of the other steps) are those within a process whereby:

1) a tubular, hollow, cylindrical metal element is provided; The tubular element is preferably a metal element, and most preferably a biologically compatible metal or metal alloy (e.g., Nitinol, titanium, surgical grade stainless steel, cobalt-nickel-chrome alloy, platinum, or the like). It dimensions are chosen on the basis of particular application needs and are not solely dependent upon the process itself. Generally the element may be within the range of 0.02 inches (0.5 mm) to 1 inch (25.4 mm) in cross-section thickness (outside diameter), with a wall thickness of from about 2 or 3 to 40% (per wall) of the cross-section thickness (or about 0.01 mm to 10.2 mm, preferably from 0.01 to 2.0 mm, more preferably from 0.015 to 1.0 mm), the hollow interior thereby being generally allowed to comprise from 20 to 94% of the linear cross-section thickness, preferably from 40 to 94% of the linear cross-section thickness.

2) the metal element is cleaned to remove oils, especially hydrocarbon or other organic oils. Typically, cleaning may include such steps as:
  i) detergent rinse (any detergent which is capable of removing oils, especially hydrocarbon and other organic oils, including skin oil, from metal surfaces without damaging the metal surface,
  ii) deionized water rinse,
  iii) acid rinse to make the surface acidic and neutralize the detergent residue, (which improves adhesion of later applied layers), using such preferably non-oxidizing acids such as HCl or solutions of acid salts, and
  iv) drying.

More abrasive treatments may be used, as well as solvent treatments to remove materials which have collected on the surface during manufacture or transportation.

3) possible coating (undercoating) of the metal element with a photosensitive or non-photosensitive layer to assist in the control of resolution in the photoresistive imaging of the subsequent photoresist imageable layer.

As shown in U.S. Pat. No. 4,672,020, the use of an undercoating or coadhered layer with a photoresist layer can adjust or improve the operation of a photoresist layer, especially where fine details are required and where such factors as undercutting are to be avoided or controlled.

4) application of a photoresist layer (e.g., by dipping, spray coating, electrophoretic coating, etc. with drying).

The photoresist layer may be applied by any of the many known film coating application techniques. Dipping and spray coating are the most common, but electrophoretic deposition is the preferred method at present in the practice of this step of the preparation of the materials in the practice of this invention. The thickness of the coating needs to be only sufficient to have the remaining relatively non-soluble pattern resist the chemical etch. The photoresist layer is preferably kept as thin as possible so that the flow of resist developer (and after resist development, the flow of etchant solution through the pattern in the resist) is not restricted. This thickness may range, for example from 10 to 200 micrometers, preferably from 10 to 150 micrometers, and most preferably between 15 or 20 to 100 micrometers). This dimension is therefore dependent upon the solvent resistance of the coating (to both the developer solvent solution and the etchant solvent solution), the strength of the developing and etching solvent. Certain resist materials tend to respond better to electrophoretic deposition than others, and manufacturers provide recommendations for their specific resists according to process applications. In the practice of the present invention, an acrylic, negative-acting photoresist, e.g., Eagle Resist from Shipley, Corp. (Alternatively a positive resist such as Shipley, Negative Resist SP2029) is the most preferred.

It may at times also be desirable to apply an aqueous removable (soluble or dispersible) coating over the surface of the photoresist, especially where the resist is an acrylic composition. Acrylic resins tend to be moisture and oxygen sensitive, preventing them from curing to their highest potential molecular weights. A water removable, temporary oxygen barrier coating (e.g., polyvinyl alcohol, polyvinyl pyrollidone, polysaccharide film, gelatin, etc.) Should be applied to the surface of the photoresist element. The thickness should be chosen mainly as a function of optical properties of the protective film, to assure that it does not absorb too much radiation which will be used during exposure, nor disrupt the laser beam sufficiently to disperse the radiation and reduce the resolution of the exposure.

Photoresist materials may be selected from amongst the broad classes of photoresists which are known in the art and are commercially available. The systems may be positive-acting (becoming more soluble where irradiated or heated) or negative-acting (becoming less soluble where irradiated or heated). The systems may be based upon polymerization or polymer cleavage or upon generation of more or less soluble species within a carrier medium (as with diazo oxides or naphthoquinones in epoxy or other polymer systems). The polymer systems useful may include a very wide variety of classes, including, but not limited to polyacrylates (including poly(meth)acrylates), polyvinyl resins, polyurethanes, epoxy resins, silane chemistry (polysilanes, polysiloxanes, etc.), phenol/formaldehyde resins (both novolaks and resols), and the like. Polymerizable systems having multiple classes of functionalities (epoxy-silanes, (meth)acrylate silanes, aminosilanes, etc.) are also generally useful. Initiator systems of many various types may also be used, such as radiation-sensitive iodonium, sulfonium, diazonium and phosphonium salts, triazine, s-triazines, biimidazoles, benzophenones, radiation-sensitive free radical photoinitiators generally, radiation-sensitive cationic initiators generally, radiation-sensitive acid generators, and the like. It is especially desirable that the substantive photoresist remaining on the cylindrical metal element after imaging and development exhibits some strong resistance to the metal etchant solution used later in the process. If the photoresist does not exhibit such strength, it may be too rapidly removed during the etching and expose metal to the etchant in undesired areas.

5) supporting the photoresist coated metal element on a rotating workpiece holder;

This is highly desirable during the process to keep the work piece (the tubular or cylindrical element) from flexing and for maintaining its position on the element. It may be desirable to have a pinning or latch element which would keep the tubular element from shifting (longitudinally or rotationally) during any rotational operation. Although the speed and forces generated by the rotation are small, any slippage would be disastrous. For example, the tubular element could have a notch or protrusion on at least one position (e.g., an end), and a post or guide could slip or fit into the notch or hole to reduce the tendency for movement of the element out of alignment. Rotation of the work piece holder should be effected by a smooth drive device (e.g., electrical, hydraulic, air pressure drive, or the like) so that wobble in the rotation is minimized or eliminated. Mechanical drives (gearing and belts drives) are useful, but can operate to more significantly limit the resolution and precision of the exposure as compared to other drive mechanisms. The support may also serve a function of protecting the interior distal backside surface from etching solutions, the support acting like a plug within the hollow interior of the cylindrical material. The tolerance between the outside diameter of the support rod and the inside diameter of the tubular metal element should be sufficient to allow the metal element to rotate and slide along the developer resistant support rod.

6) positioning the photoresist coated metal element in the light path of a laser imaging device, the laser imaging device having a laser source and an optical aperture mask, with the optical aperture mask being located between the laser source and the metal element;

The gross positioning of this step may be effected by placing the tubular element on the work piece holder, placing the work piece on a support rod within a rotation effecting system and the like on the distal side of the aperture mask from the laser source. The actual positioning must be more precisely effected during the processing or at least during the initial set-up for the process. For example, placement and alignment of the work piece may be automatically evaluated by sensing devices such as infrared sensors, reflecting/detection systems, interferometric detectors or position detectors. Once the workpiece is found to be in proper alignment, the process may then proceed on a basis of essentially only rotational position awareness and detection. That is, once the axis of the workpiece (and/or the support) have been assured to be accurate, and the radiation beam is focused on the correct spatial position, rotation (and longitudinal movement) of the cylinder and longitudinal movement of the cylinder that needs to be accurately changed to position the surface of the longitudinal element at the appropriate focal plane for the laser beam after is has passed through the aperture openings.

The rotational position of the surface of the metal element with the photoresistive coating thereon must be coordinated with the laser emissions from the laser source. A computer preferably should be programmed to indicate the proper pulse or emission time, or the proper shutter operation time and sequence (if a physical shutter is used) to have the laser imaging system (creating a latent image on the photosensitive resist material) coordinate its activity with the proper positioning of the photoresist material coated metal element. Because the laser radiation moves so quickly, especially relative to the dimensions of the system, the photosensitive coated metal element may effectively move continuously and be exposed whenever the appropriate spot is to be irradiated, although it may be stopped at particular positions if desired. The laser may be pulsed accordingly, the shutter may be opened and closed accordingly, or any other measure taken to time the passage of the radiation through the aperture openings and time the impact of the radiation on the appropriate surface position.

The software operating the system should operate on a basis of establishing an initial position on the cylinder (which may be determined as an angular orientation of the cylinder, such as artificially designating a position on the rotation of the cylinder [or its support] as zero or some other value). As the cylinder is rotated (either continuously or in a step-wise fashion, e.g., with increments of between 5 and 90 degree rotations of the cylinder, preferably between 20 and 80 degrees, the pulses of the laser are timed to pass through the apertures in the aperture mask so that the position of the stenciled light (the radiation or light from the laser which has been shaped by the aperture) is appropriately targeted on the surface of the photoresist. As the speed and duration of the laser pulse (e.g., the speed of light with pulse times of for example 3 to 100 nanoseconds, preferably 3 to 20 ns) make the distances and the rotational speeds which can be used (e.g., 1 to 1,000 revolutions per minute, or even more) insignificant with respect to the resolution of the image exposure on the surface.

More significant than the speed of revolution of the cylindrical element is the percentage of the arcuate surface of the cylindrical substrate which is covered by the exposure. As the radiation of the exposure strikes further up the latitude of the cross-section with respect to the surface of the cylinder closest to the laser source (e.g., where the laser would strike the cylinder surface at a ninety degree angle of incidence), the angle of incidence increases, there is a greater tendency for reflection of the radiation off the surface, a greater tendency for refraction of the radiation passing through the photoresist (or any protective cover layer), which would weaken or vary the exposure levels of the radiation on the photoresist. Even though exposure levels tend to be used which are at least five times higher, preferably at least 10 times higher, and more preferably at least 20 times higher than the radiation levels needed to fully initiate or cure the photoresist composition, the angle of incidence can still be important from a sensitometric position. In addition, as the angularity of the exposure changes, the angularity of the exposed resist material changes. Rather than having a latent image which has wall which are perpendicular to the surface of the cylinder (e.g., radially emanating), the walls will tend to be more angular. This affects the shape and even location of the bottom of developed openings in the resist, and therefore would affect the shape of the etched pattern in the cylindrical element and the orientation of the walls of the etched pattern.

7) exposing through different sections of the aperture mask, each section having a different image or portion of an image aperture thereon (and optionally, but preferably, the aperture holes or patterns having shapes and sizes which compensate for spread of the image on the surface or which do not have a 1:1 correspondence for radiation spread on the surface (with the aperture size being >1:1 with respect to the actual intended image size). The aperture is usually moved only vertically, with the individual patterns through which exposure is to be made being oriented in a preferably linear arrangement within the aperture mask. In this way, the aperture mask may be moved in only one direction as it is coordinated with the rotation of the tube element and the emissions of the laser. The arrangement may be other than linear with motion control in at least two dimensions (vertically and horizontally) then being necessary. That arrangement would tend to allow for a larger number of available patterns on the aperture mask.

Figure 2:
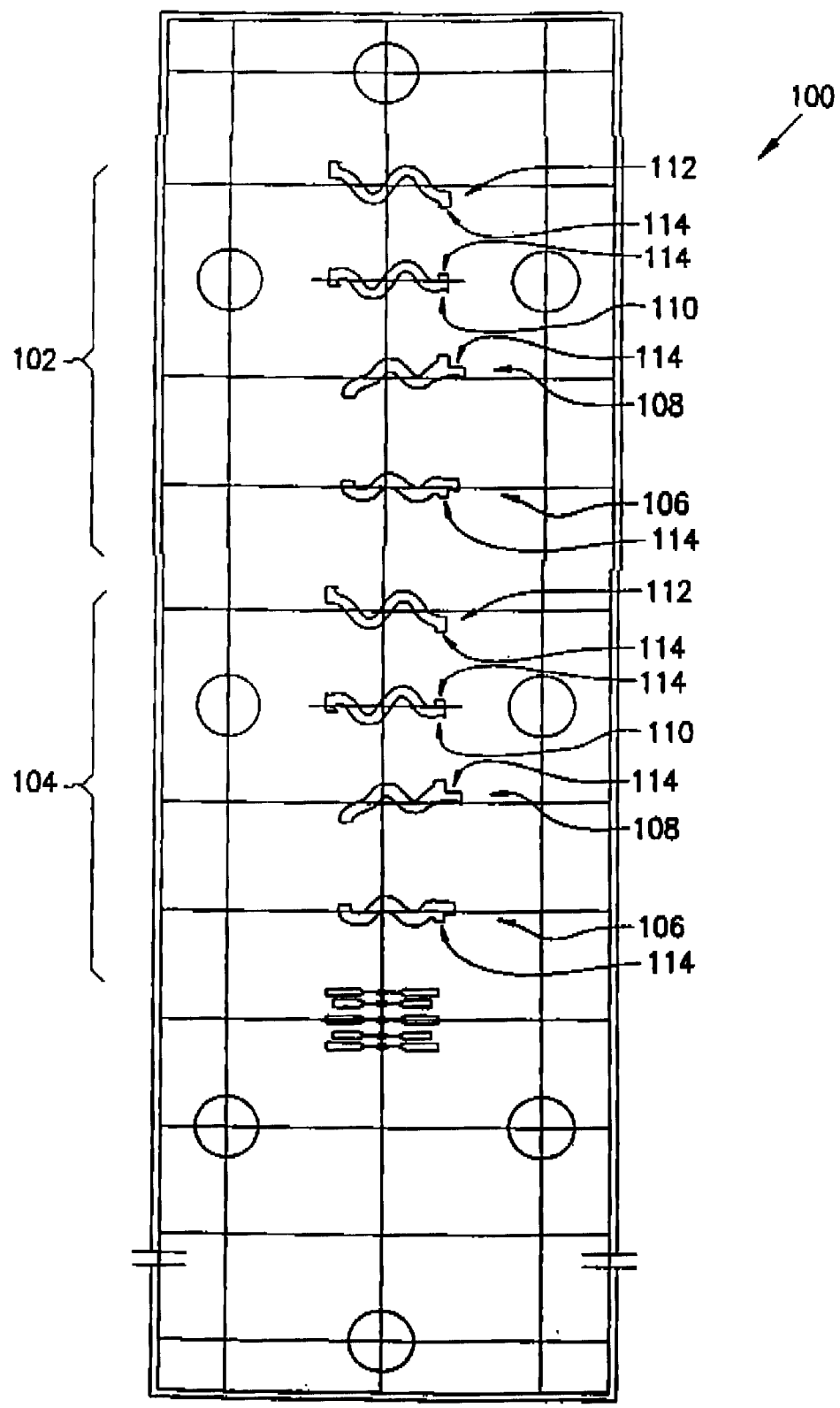
FIG. 2 shows an aperture mask for use with the present invention.
Figure 4:
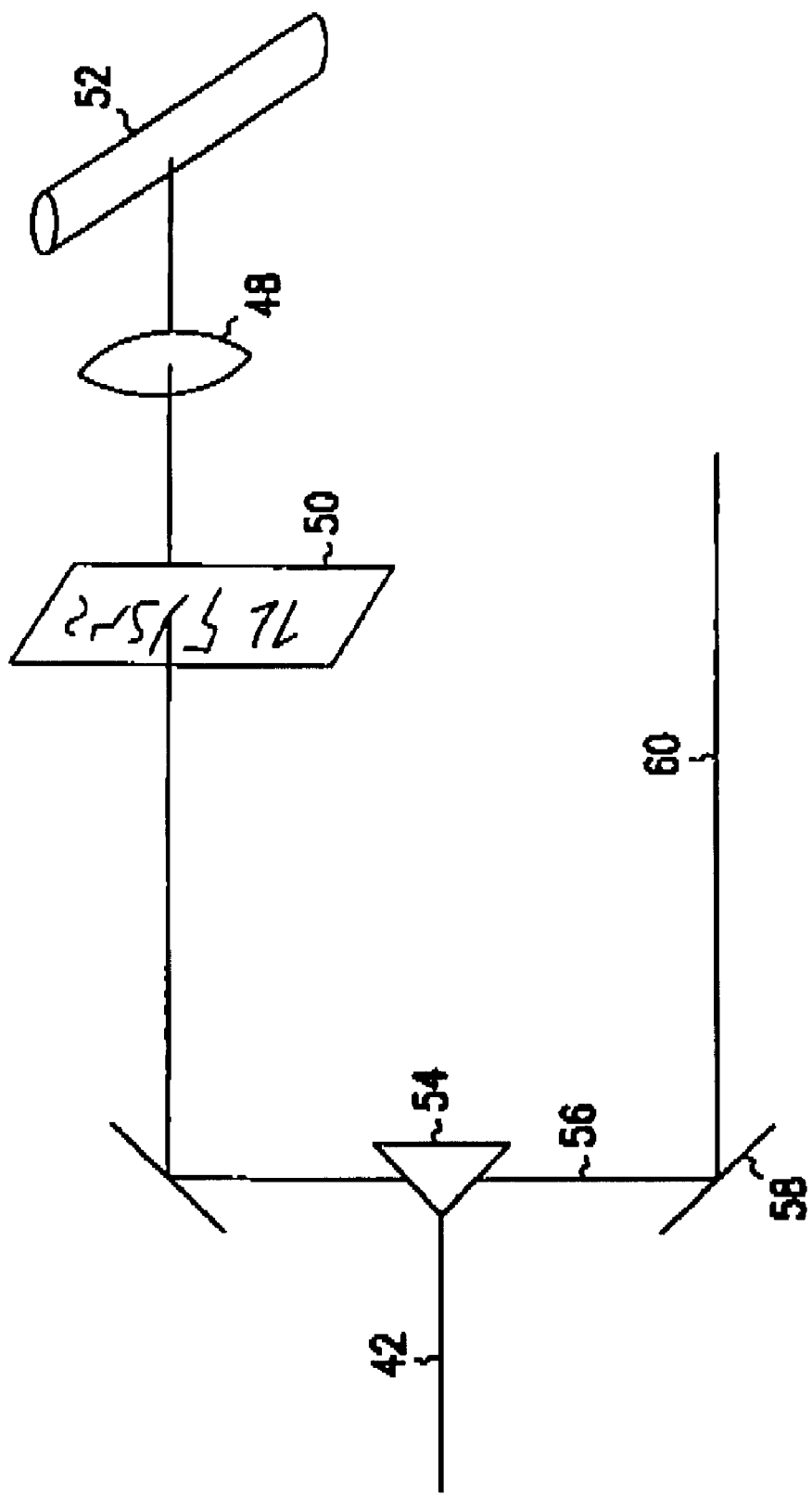
FIG. 4 of the present invention shows a flow diagram of the process of the present invention.

The spot size of the laser (e.g., the diameter of a circular spot or the longest axis of an elliptical spot) should be greater than the longest dimension of the apertures in the mask. The longest dimension of the aperture should also correspond with the greatest size dimension of the spot. That is, correspond with the One specifically unique aspect of the present invention in this particular step is the use of segments of patterns, rather than complete patterns of exposure in the aperture mask. It is typical, as shown in FIG. 21b of WO 97/42910, to have a single type of aperture hole (or a complete pattern in contact with the surface as with a conventional stencil or exposure mask) through which the exposure of the radiation is projected. As shown in FIG. 2, an aperture mask 100 is shown with a pattern of aperture holes 106, 108, 110, and 112 of which at least two are significantly different in size and shape (usually most or all may be different). Laser radiation (e.g., ultraviolet, visible or infrared) 42 (FIG. 4) passes through one of the openings 106 in the aperture mask 100 and exposes a latent image (not shown) corresponding to the shape of the opening 106 on the surface of the photosensitive (photoresist) coated tubular element 52 (FIG. 4). The position of the latent image is formed at a desired relationship to an existing latent image (not shown). It is to be noted that the respective latent image is not necessarily the same size as the aperture hole through which the latent image was exposed. As compared to the use of a mask in contact with a surface, this type of exposure is believed to provide resolution advantages even with the added distance between the mask and the surface to be imaged. Considerations of spreading, edge effects from the aperture mask, and the like can be readily predicted in this system and accommodated for in the process.

FIG. 1 of the present invention shows a vein 1 having a catheter 2 therein. The catheter 2 has within its lumen 3, a pushwire 11 and a stent 10. The stent 10 has open areas 12 which are defined by a sinusoidal pattern of etched metal 13. The stent 10 is typically pushed out of the opening 6 in the catheter 2 and then allowed or forced to expand against the inner surface 5 of the vein. The dimensions of a stent will be dependent upon the particular use to which it is put and the particular vasculature or body part in which it is used. Intracranial stents would be quite small, both in gross diameter and metal thickness, while catheters for ducts and the like from the liver or gall bladder or pancreas would be relatively large. For example, the gaps within a stent (the space between the metal structural material) may be from 0.5 to 7 mils, depending on the area of use, with typical vascular stents having gaps between 2 to 5 mils and preferably from 2.5 to 4.5 mils. The thickness of the structural metal may be from 3 to 10 mils. The practice of the present invention provides a unique capability of accurately providing relatively thin metal stents, e.g., those having metal thicknesses of less than 6 mils, preferably less than 5 mils, and even from 2 to 4.5 mils, with high resolution and clean edges. This is extremely difficult to effect, and only with the practice of the present invention is this capability known to be provided. One of the difficulties with the prior art techniques is the fact that the chemical etch tends to leave rough surfaces. The thin metal walls of the stent do not allow any significant mechanical smoothing after the etch because of the fragile nature of the porous and open nature of the stent. The width of the metal in the stent (which describes the gaps or openings in the stent) are again determined by the design and use of the final stent product. These gaps are limited only by the resolution of the imaging technology, the strength of the metal, and the quality of the chemical etch. The present invention optimizes these qualities so that metal widths of less than 2 mils, even less than 1.5 mils, can be produced. It is preferred that the metal width be between 0.5 to 10 mils, preferably between 1 and 8 mils, and more preferably between 1.5 and 4, 5 or 6 mils.

FIG. 4 of the present invention shows a flow diagram of the process with an optical lens 48 present between the aperture mask 50 and the cylindrical object 52.

One feature that is desirable in the practice of laser imaging exposure is the fact that the original laser beam may be split or reflected off a rotating mirror at different targets in sequence or contemporaneously. That is, a single beam 42 may be split to image two distinct cylindrical objects (either on the same support at different longitudinal locations or on a separate, preferably parallel support). As shown in FIG. 4, a beam splitter 54 provides a second beam 56 which is then reflected off a second optical mirror 58 as an independent, but similarly pulsed light beam 60 which may then be used in an independent imaging process. The split beam 60 may pass through different aperture masks (not shown) or may pass through different openings in the same aperture mask. To effect the latter, it would be desirable to provide multiple sets of aperture holes on the mask, each set being capable of providing the necessary individual segments for the completed pattern on a cylindrical element.

The spot size, as mentioned earlier should be of somewhat greater maximum dimension than the greatest dimension of the largest aperture to be used in the imaging process. This means, in the practice of the present invention that the spot size may be greater than 1 or 1.5 cm with correspondingly smaller individual apertures. Each of the apertures provides an individual field of exposure on the photoresist surface which adds up to the final composite. The individual fields should be exposed so as to have portions which slightly overlap at zones where the fields overlap. It is preferred that the individual fields overlap along a linear dimension where the fields abut by at least 0.03 mm, preferably at least 0.01 to 0.03 m.m., and most preferably by at least 0.005–0.03 mm. This overlap allows for the photoresist to be assured of having the abutting areas sufficiently exposed (in a negative-acting imaging resist system) to assure complete hardening or (in the case of positive-acting resist systems) to assure complete reduction in solubility.

FIG. 2 shows an example of an aperture mask 100 which can provide this function. The mask 100 comprises two distinct sets of apertures 102 and 104. The two sets of apertures 102 and 104 have the same pattern of individual apertures 106, 108, 110 and 112. By having two supported cylinders (not shown) synchronized in their rotation, a split beam may image essentially identical patterns in the two different cylinders by passing the beam through the two sets of apertures 102 and 104. Extended feet 114 are shown, these feet 114 extending from one imaged area into another imaged area to assure complete exposure at the interfaces of the exposed images.

The latent image is imposed upon the photosensitive coating by incrementally piecing segment of images together according to the openings in the aperture mask. Rather than having to alter spot sizes at the source of the laser, using the same laser spot shape and size for a variety of patterns (which means a greater number of exposures and greater likelihood of spillover imaging), or some other standard mask variation, the provision and exposure through a variety of aperture openings of different shapes which have been specifically designed and selected to provide the individual shapes and areas which can be used to generate the precise pattern needed in the etched article. The computer program controls the passage of the radiation through the openings in the aperture mask both with respect to time and position (of the appropriate mask opening). The program would operate by:

a) assigning one point as a starting point or reference point on a surface of the cylindrical photoresist coated metal element, b) identifying a specific pattern of exposure desired on the surface of a target (the cylindrical, photoresist coated metal element), c) identifying a series of patterns of aperture openings available to expose the surface of the target, d) while said surface of the target, signaling a laser imaging system to provide exposing radiation to the surface of the target (e.g., either by pulsing the laser according to a timed distribution, or by operating an associated device (e.g., a shutter or lens) at selected times, e) directing radiation through one of a series of openings in an aperture mask, and imaging a pattern on the surface of the target by using more than one opening (at least two openings, up to as many openings as desired, such as twenty or more) in the aperture mask to shape the exposure pattern on the surface of the target, at least two different openings of different shapes and/or size being used in this exposure step, and f) while said cylindrical element is moving horizontally (parallel to its longitudinal axis) as well as rotationally, identifying the appropriate exposure signals to be sent to the laser imaging system to cause the pattern to form over both circumferential and longitudinal surfaces on the cylindrical metal element.

8) rotating the photoresist to present different regions of the photoresist coated surface of the metal element towards the aperture mask, with the different sections of the photoresist coated surface being exposed as desired;

As noted in the previous step, the cylindrical metal element is rotated to present its surface to the exposing laser beam. This rotation must be smoothly performed coordinated with the timing of the laser. Additionally, the trajectory of the laser beam or the position of the aperture mask must be adjusted to impact the surface appropriately. The beam may be directed towards the surface by altering the position of guiding mirrors which typically direct the beam from the laser emitter to the aperture. By controllably altering the angle and/or position of the mirror, the radiation may be directed through the appropriate opening in the aperture to the proper position on the surface of the photosensitive coating. The mask itself may also be reoriented appropriately while the beam remains steady. Exposing radiation may often intentionally impact solid portions of the aperture mask, as the metal is generally impervious to the energy level of this exposing (as opposed to ablating) laser radiation. The rotation should be effected in a manner which minimizes chatter, stutter, wobble or other irregular variations in the uniformity of the movement of the surface of the cylindrical element and resist. Non-belt driven or non-gear driven assemblies, such as hydraulic or electromagnetic direct or torque drives are preferred for this purpose.

9) preferably rotating the element continuously, with the exposure timed through the apertures by one or more of a computer program identifying the position of the metal element, pulsing of the laser, shutter control of the laser beam, and laser spot location/overlap as exposure compensation for the angularity of the surface being exposed, and forming a pattern of material from the photoresist material which is differentially soluble in a solvent as between exposed and unexposed areas. As noted earlier, the rotation of the element may be done episodically rather than continuously (in a step-by-step manner). It is preferred, however, that the cylindrical element be rotated continuously during imaging for processing speed.

Again, as noted earlier, one of the advantages of the system is to keep the metal element rotating continually so that a nearly continuous process can be performed on each metal element. The metal element may comprise a long section of metal tubing so that a number of stents may be imaged on the single tube and then the tube cut into appropriate segments, each of which is a stent.

10) baking or burning of the resist to make the solubility differences between exposed and unexposed areas more pronounced, toughening the less soluble component, increasing surface adherence of the less soluble component of the pattern to the metal surface, etc.;.

This is a step often done in the positive printing plate art, which is a type of resist or differential surface tension imaging system. It is not known to be used in the photolithographic imaging and etching of stents as practiced in the present invention. The burn-in may be affected by the application of heat, the application of UV, visible, or infrared radiation to which the photosensitive media was sensitive, or to infrared radiation as an alternative source of heat. The energy additions for the burn-in may also be combined. The burning step may be performed after the development step (which is listed herein as step 11).

11) developing. removing the more soluble areas of materials by contact with a developing solution which is more active towards exposed or unexposed areas than to unexposed versus exposed areas, respectively;

It is preferred that this contact be an active contact, that is a contact with some kinetic activity as by stirring a solution in which the element has been placed, swishing the element through a solution, spraying the solution against the surface, or the like); an optional scumming (scum removal) treatment with optical powder, pumice scrub, or the like to mildly remove or abrade away scumming to make the surface to be chemically etched more uniform in properties can be performed about here in the sequence of steps. It is to be noted that the removal of residual resist material within the finely developed image areas by the use of particulate materials in a slurry (e.g., particles having an average particle diameter of less than 25 microns or less than 20 microns, preferably an average particle diameter of less than 10 microns with a particle size variation of less than 25 number percent of the particles having a deviation above the average particle size of more than 30% (and preferably no more than 25%). It is also preferred to use a very fine slurry of particulates with average particles sizes less than 5, preferably less than 3 and even less than 2 microns in average particle size diameter. The particulate slurries are applied to the developed resist image with mild agitation or pressure and then followed with a rinsing step (e.g., step 12, following). This has been found to provide a sharper image, which is not believed to have been disclosed within the photoresist imaging art for non-flat (e.g., three dimensional or especially cylindrical) resist imaging.

There are also additional particle properties desirable in the materials used for the slurries of the present invention. For example, it is preferred that the particles have a hardness of at least 8 Mohs (preferably >8.5, >9 or more), a Knoop hardness of at least 1900, preferably at least 2000, and more preferably 2100 or more, insolubility in water or organic solvents, and being non-polymerizable under working conditions. A bulk density of greater than 1.4 $g/m^3$, preferably grater than 1.5 $g/m^3$, and most preferably greater than 1.6 $g/m^3$, is desirable. Such abrasive are typically prepared from inorganic oxides, inorganic sulfides, inorganic nitrides, inorganic sulfides and the like. Typical examples of these are aluminum oxides, aluminum sulfide, titanium oxide, titanium sulfide, and silicon oxide or silicon sulfide, alone or in mixtures. Minor amount of other oxides or sulfides (e.g., $Na_2O$, MgO and CaO) may be present in minor amounts in the composition, these latter materials being generally too soft or tending to undesirable solubility.

12) rinsing and drying the developer solution off the metal element with a patterned resist coating on it. Rinsing is done with aqueous solutions, including deionized water or water with mild detergents or surface active agents to assist in material removal from the developed surface.

As an independent step in this removal of resist from the developed region, the present invention has found that further stress can be placed on the side walls and features of the developed areas by the use of fine abrasive powder in slurries or dispersions, as opposed to merely liquid washing materials. The slurry or powder (such as the use of optical polishing powders and ultrafine abrasive grit) improves the removal of resist material from the edges of the developed areas adjacent the metal cylinder surface and the remaining side walls of the resist layer. This has not been disclosed before and has shown particular advantages in the cleaning of developed areas in three-dimensional resist images and particularly in cylindrical etched elements.

13) chemically etching the exposed surface of the metal element through the open pattern exposed and developed in the photoresist coating on the metal element.

The metal tube may be rotated in the etch solution with mild stirring or agitation of the solution to get a uniform etch on all sides of the element (e.g., by placing the metal element on a preferably non-etchable support element or rod which is rotated); again, a spray of the chemical etch, rather than immersion, appears to be uniquely beneficial to the formation of the cylindrical patterned elements of the present invention. Rather strong etch solution may have to be used, depending most particularly upon the nature of the metal, as with nickel containing metals requiring stronger and more frequently replenished etchant solutions. For example, a typical etch will contain ferric chloride solution. Additional materials may include hydrofluoric acid, nitric acid, ammonium difluoride, hydrochloric acid (as a trace from the ferric chloride or as an additive material). It has been found to be desirable to operate with a Baume of 47°±8 degrees. At the higher Baume levels, especially with ferric chloride, it is necessary to elevate the temperature of the etch to between 110 and 150° F., preferably between 115 and 135° F. This elevated temperature in combination with Baume levels above 47.5°, usually above 47.5 and below 56° Baume and especially between 48 and 53° Baume, is itself novel in three dimensional etching;

Even the provision of the high Baume' etchant solutions is not a trivial task and its provision is not reported in the literature. Because the solutions are of such a high concentration of etchant and adjuvant materials, it is very difficult to merely mix the high concentrations into a solution at room temperature or even at elevated temperature. It has been found to be most advantageous and convenient in the practice of the present invention to provide a typical etch solution with a Baume' of 47 or less and then to controllably evaporate liquid (water) out of the solution at room temperature or at an elevated temperature (e.g., 25–90° C., 72 to 186° F.) to provide the proper concentration of materials. It is particularly preferred to perform this at elevated temperatures (e.g., 35–90° C., preferably 40–75 or 80° C.) to assure that the materials in the etchant solution do not crystallize out. It is desirable during the practice of the invention, both in the formation of the compositions and the in the etching step itself to minimize any crystallization, so that less than 2% by weight of solids in the solution crystallize out of the solution during that specific step (either during the compounding or particularly during the etching).

The high specific gravity of the etchant solution which is measured on the Baume' scale is surprising in its ability to perform a higher quality, more smooth surface etch than traditional low Baume' etching solutions. Even though the concentration of active agents is higher in the higher Baume' solutions tends to be higher than in the traditional solutions with a Baume' of less than 47.5 (e.g., 47 and lower), the etch is slower (a lower rate or material dissolution or etching), but the quality of the etch (as visually and statistically determined in the roughness of the surface left after etching) is much higher. This is particularly beneficial, if not critical in the manufacture of small medical devices such as catheters and stents. Because these devices must often be small and have thin walls, reduced quality in the etch itself can cause increased waste of materials (which are quite expensive), require attempts at salvaging rough items (which is expensive and difficult, again due to the small and thin nature of the material), and can lead to defects in the device which are not readily found in ordinary inspection (e.g., structural defects in the orientation, structure or crystallinity of the metal materials). The fact that the use of higher Baume' etchant solutions, irrespective of the chemical nature of the etchant solution, can provide this effect, is a significant advance in the manufacture of small metallic articles. This is particularly true where the surface of the article being etched is three dimensional, as opposed to etching on a flat surface. Even though the higher Baume' (specific gravity of greater than 47 degrees Baume') increases the quality of etching on such flat surfaces, the use of these solutions and the degree of benefit on the etching of surfaces, especially where all the exterior surfaces of an element is being developed, which surfaces are not all within a single plane, has been found in the practice of the present invention to be uniquely beneficial. As noted earlier, the etch over the cylindrical surface is not necessarily always radial (from the center of the cylinder) or not always perpendicular to the underlying surface (because of the angle of exposure and development of the resist). These unavoidable characteristics in the object or the resist provide an innate limitation on the quality of the resist image and the need for increased quality in the physics and control of the etch itself becomes more critical. This is even more critical in medical devices of small dimensions where etch failure is potentially fatal, injurious and expensive.

To define and distinguish a threedimensional surface from a two dimensional surface, the following should be considered. A two-dimensional surface lies essentially within a single plane or occupies a complete rectangular volume (considering the length, width and depth, for example, of a layer coated on a flat surface). The extension of the paths of the etch through the substrate will consist essentially of parallel paths of extension. A three-dimensional etch surface will have etch paths which are not parallel to each other. As when etching a cylinder with either a square, triangular or rectangular cross-section, many of the paths of the etch in the substrate will radiate away from each other in a non-parallel orientation. It would be common with three-dimensional articles that do not have predominantly flat faces (as with the triangular or rectangular cross-sections) that the paths of the openings in the resist layer may have parallel sides on the walls of the developed resist, but do not have all walls perpendicular to the underlying surface to be subsequently etched.

14) rinse away the chemical etch and/or neutralize the etching solution;

15) strip the remaining photoresist (relatively insoluble photoresist as compared to the relatively soluble photoresist that was removed) from the etched element (e.g., with an organic solvent such as isopropanol). With a positive-acting photoresist, the residue may be removed by exposing the remaining coating and developing the exposed (and solubility-increased) material.

16) remove the etched element from the support and pack it for transportation.

The process and materials of the present invention also encompasses techniques for the photolithographic and chemical etching of circuitry onto or into medical inserts such as catheters or stents. The process for this embodiment of the invention would encompass the formation of a partial or complete metal (conductive) coating on the surface of a catheter or stent. It would be preferred if the catheter or stent had a sacrificial layer (preferably non-conductive) under the metal layer. The catheter or stent material should be resistant to an etch useful on the metal coating. The tubular element (the catheter or stent) with the metal coating on it, is coated, imaged and resist developed according to the process described above. That imaging, however, would be in the form of providing negative images (exposed areas for development) of desired electrical patterns (e.g., resistive heating elements, conducting leads, etc.), circuitry, Magnetic Resonance Imaging coils, or the like. After development of the resist layer, the exposed metal can then be etched to provide the positive structure of the desired conductive (metallic) pattern on the catheter or stent. All of the steps and features of the present invention can be used as desired in the practice of such electronic or circuitry preparation on catheters and stents.

The following information describes and circumscribes the best mode of practicing the invention.

I. In the selection of raw materials for stents, the metal tubing is preferably a high quality, uniform composition and uniform thickness metal tube. An example of the preferred metals are Nitinol or 316LSS fully annealed stainless steel. The preferred range of dimensions for tubing used in the present invention comprises:
  ID (Inside Diameter)=0.01 to 0.5 cm, preferably about 0.051 inch (0.13 cm)
  Wall thickness 0.002–0.3 cm, preferably 0.0025–0.004 inches (0.0066–0.11 cm)
  OD (Outside Diameter)=0.1 cm to 0.2 cm, preferably 0.056 in.–0.059 in. (0.14–0.15 cm)
  Length=0.1 to 1.5 m, preferably about 2 ft (0.61 m)
  Photoresist
    1. Electrodeposited Resist, Shipley Co. Negative-acting photoresist, aqueous-based.
    2. The process is equally amendable to the use of positive resist, such as Shipley SP2029.

II. Tube Cutting Prior to Etching
  A. Tubing may be cut into shorter (e.g., 6.25 inch, 15.9 cm) lengths using a rotating blade cutter III. Pre-cleaning:
  A. Handling Devices Used
    1. Hand held screened basket to support elements without compressive damage
  B. Sprex™ Cleaner Dip Tank
    1. Bath Composition: ~1.5 wt % Sprex™ A.C. powder Balance: city water; Sprex is Du Boise Sprex™ A.C. Cleaner, a caustic-based detergent
    2. Process settings: Temp=145 to 180 degrees F., preferably about 166° F. Time=2–5 minutes
    3. Parts are placed in a screened basket and dipped in the tank for 2–5 minutes, then removed.
  C. DI Water Rinse
    1. De-ionized water spray, room temperature, spray pressure of 5–8 psi, time=5–30 seconds, preferably about 20 seconds
    2. Tubes are hand-held in spray at various angles; some spray is directed into the interior of the tubes such that visible flow can be seen exiting the opposite end of the tube.
  D. HCl Acid Dip Tank
    1. Bath Composition: 25% HCl acid reagent, 36% HCl Balance city water
    2. Process Settings: Temp=60–80 degrees F., preferably about 70° F. Time=5–30 seconds, preferably about 20 seconds
    3. Parts are hand-held in tank
  E. DI water rinse as per step C
  F. Dry Box
    1. Process Settings: Temp=115 to 145° F., preferably 130° F. Time=until dry, generally 10–15 minutes
    2. Parts are laid on absorbent sheets such as Kimwipes™, often air is blown through the interior halfway through the drying. Pressurized air nozzle, hand-held IV. Resist Coating—currently performed by electrophoretic deposition of resist polymer composition,
  A. Electro-deposited negative photoresist
  B. Performed in a tank
  C. Resist thickness at the end of the element is about 10 to 150 micrometers.

VI. Resist Drying

VII. Resist Imaging—This is described thoroughly above.
  A. Equipment
    1. Laser source—pulsed laser, e.g., excimer laser
    2. Optical focusing and focussing mirrors
    3. Optical Aperture Mask—made by Buckbee-Mears St. Paul
    4. Tube positioning fixture
      a. Silicon supporting element with a hole drilled into a face thereof which matches the OD of metal tube closely, and also has a piece taken out of the side where the laser is directed.
    5. Motion Control Systems
      a. For tube: A motivating system, e.g., rotational assembly, attaches to one end of the support for the tube. The assembly directs the tube rotationally (turning about its longitudinal axis) and longitudinally, moving the supporting element parallel to the longitudinal axis. The system is preferably operated continuously (rotated and translated longitudinally) throughout imaging.
  b. For aperture mask: currently connects to S5 aperture mask (thickness=0.001 to 0.005 inches [0.025 to 0.076 mm], preferably about 0.002 in. [0.051 mm]) moves vertically on a screw system, but hydraulic, or electrically driven pulley, torque, or magnetic system may also be used. A wheel aperture mask which would rotate has also been investigated. It is to be noted that in its preferred operation, the aperture mask only moves periodically.
  c. A computer controls both motion systems (that for the tube and that for the aperture); and could also control the laser shutter as well.

VII. Resist Developing
  A. Spray developing, with the resist developer being sprayed against all cylinder surfaces of the tube. The spray may be directed from all areas around the supporting tube as it is carried through a spray chamber and/or the tube may be turned in a chamber with fixed spray heads. The resist developer may also be applied by pad wiping application, dip application with some agitation within or after removal from the dip tank, and the like.

VIII. Post-developing Burn-In/Re-Exposure of Resist
  A. A variety of burn-in methods were experimented with; including no burn-in.
  B. Conditions Tried
    1. Pizza oven: temp setting=610° F., time=25–30 seconds
    2. Lower Temperature, IR heating: temp setting= 450° F., speed setting tube taped to a clip and hung on conveyor through vertical IR banks
    3. Higher Temperature IR oven: temp setting=1150° F., speed setting=25–35 Tubes ran as above; note this is a different machine than the lower T IR
    4. None (no burn-in)
    5. Dry box; temp=150° F., time=90 minutes, tubing hung in dry box taped to clips IX. Resist Repair and spotting
  A. This process is manually performed and is intended to be eliminated in the future. It is done to improve the quality of some of the developed prints. Not all samples were spotted.
  B. Spotting material is hydrocarbon based; applied with a paintbrush with tube under magnification, to repair and fill in any handling scratches, pin holes, or other defects.

X. Etching
  A. Equipment
    1. Rotary Spray Etches
      a. constructed of etch resistant materials (Titanium, PVC)
      b. oscillating spray nozzles
      c. rotating flat
      d. further rotation of tube
      e. city water hose rinse
      f. light table for visual inspection
    2. Tube Handling Fixture
      a. PVC round flat-modified
      b. Titanium support rod supporting the metal tube to be etched fits on both ends of the tube and must penetrate into the opening into the tube sufficiently to maintain support of the tube, e.g., ~0.02 to 0.90 inches, preferably about 0.045" into holes drilled in 2 PVC support bars. The fit is loose enough to allow for turning of the tubular metal about the support rod, but without sufficient clearance to allow unrestricted flow of etchant between the rod and the supported metal tube.
      c. An etch resistant gear-like (PVC pinwheel) is attached (permanently) to the Titanium rod so that the natural motion of the etchant spray will cause the Ti rod to rotate as the pinwheel is turned. The metal tubes (e.g., the stainless steel tubes) fit somewhat snugly onto the Ti rod; but some clearance exists, which allows for slipping the tubes on and the etched pieces off with minimal damage.
    3. Rough Inspection Equipment (for Etch Time determined)
      a. Light Table
      b. 40× microscope
      c. PVC piece, 3/4" thick, with channel drilled in the middle. This provides a support for the microscope so that when the flat is laid on the light the Ti rod and sample lie deep in a channel near the top surface of the PVC piece. Then one can hold the microscope steady, adjust it easier, and even rotate the tube more easily.
  B. Etch Process Set Points—these are the most commonly used parameters for this application
    1. Temperature=115–130° F.
    2. Baume=48°B, ±7% (preferably for difficult to etch metals, between 47.5 and 55 Baume', more preferably between 48 and 55 Baume'.
    3. Spray Pressure=10–25 psi; front & back nozzles
    4. Spray oscillation speed=60 (setting on dial), approximately 8 to 40 sweeps or cycles (up and down) of the nozzle per minute.
    5. Flat rotation speed setting=60 (e.g., the approximately 1 meter flat moves at a top edge speed between 0.1 or 1 and 30 cm/sec through the spray area, more preferably between 1 and 5 cm/sec.)
    6. HCL Acid level=<1%
    7. Etch time=10–14 minutes, dependent upon tube wall thickness, etch composition and parameters, and other issues.
  C. Pre-Etch Scumming
    1. This optimizes the uniformity of the exposed metal surface on the developed prints. Performed with the tubes already placed on the titanium rods, hand-done at present.
    2. Scumming with Optical Powder—rubbed w/cotton
    3. Scumming with Lan-O-Sheen™—rubbed w/cotton
    4. Electrocleaning of metal surface XII. Stripping and Cleaning
  A. Handling Fixtures
    1. Thin Stainless steel rods
      a. Individual etched pieces are removed from the carrier and handled using a very small stainless steel (often referred to herein as "SS") rod, which fits loosely enough inside the cylinders that fluid can flow freely on the inside surface. The tubes are stripped, cleaned, and dried while on this rod, then placed back into the carrier.

b. Thus far the rods have been hand-held, 1 rod at-a-time, and hung in the tanks with bulldog clips individually as well. Fixtures containing multiple thin SS rods are easily produced.
B. Both compositions: Stripper=RD68 and 30% RD68 (ChemClean CULX™ Cleaner) (15% by KOH by volume) balance city water
C. Process Settings: Temp=160–180° F., preferably about 175° F. Time=3–10 minutes, preferably about 5 minutes
D. DI Water Rinse
   1. Similar to Process C; DI Spray is directed such that the resist is blown off of the tube.
E. Isopropyl Alcohol Rinse
Room temperature IPA bath used as a final clean, also to aid in the drying
XIII. Inspection, Packaging
A. Inspection has been performed using hand-held microscopes and stereoscopes.
B. Packaging thus far has been in clear plastic tubes with caps on both ends.

The process of the invention, including the photoresist imaging aspects may include, for example, the steps of:

a) coating a hollow metal tube with a photosensitive resist coating layer;

b) supporting the metal tube on a (preferably rotatable) support;

c) providing radiation comprising wavelengths of radiation to which the photosensitive resist coating layer is sensitive (the radiation being a laser, flash exposure, focussed beam, lamp exposure, continuous exposure or the like);

d) directing the radiation onto the surface of the resist layer in a pattern (negative or positive, depending upon the nature of the resist) which defines the shape of the resist which is to be left on the hollow tube surface. This patterned distribution of radiation may be effected by positioning of small laser spots in the desired pattern (as is typically done with the exposure of printing plates, especially gravure plates, a form of photoresist coating), passing said radiation (either as a laser beam, focussed beam or open illumination from a lamp) through at least a first opening in an aperture mask which is not in contact with the coated hollow tube to expose an area on the surface of the photoresist coating on the metal tube and alter its relative solubility. A focussing lens may be present after of before the aperture mask or other radiation which is directed at the surface of the resist.

The rotatable support is rotated to rotate the surface of the photoresist layer, and then additional radiation (usually from the same source, although a separate source, e.g., second light emitting diode or laser may be used) comprising wavelengths of radiation to which the photosensitive resist coating layer is sensitive is similarly or additionally directed to the surface of the photoresist coating to be exposed. This radiation, when used with an aperture mask, may pass through the first opening (if the pattern can be used a second time in the exposure of the photoresist coating on the surface to be an additive part of the final image desired) or through a second opening in said aperture mask. The shape of the second opening preferably being different than the shape of the first opening in said aperture mask. The exposure and timing of the position of the openings in the aperture mask and the passage of said focussed beams through said openings so that a desired pattern of exposure of the surface of said photoresist coating layer is formed, said desired pattern comprising combinations of areas exposed through at least said first opening and said second opening;

h) washing said photoresist coating layer having the desired pattern of exposure thereon with a developer which will develop either the exposed desired pattern of photoresist coating layer more readily than unexposed areas of the photoresist coating layer or developed the unexposed areas of the photoresist coating layer more readily than the desired pattern of irradiated photoresist coating layer to assist in removing areas of the photoresist coating layer while leaving other areas of the photoresist coating layer on a surface of the hollow metal tube in a negative image of said desired pattern or in said desired pattern, thereby forming a cylindrical element with a physically exposed pattern of metal underneath the photoresist coating layer;

i) transferring said metal tube with a physically exposed pattern of metal onto a chemical etch resistant support element;

j) contacting the physically exposed pattern of metal with a solution capable of etching the metal of the metal of the metal tube so that said metal is etched away from physically exposed surfaces of the metal tube and openings in the metal tube corresponding to the pattern of physically exposed metal are created in the metal tube element;

k) removing said metal tube from said chemical etch resistant support element.

The process may include contacting the physically exposed surface of the metal tubular element with a solution capable of etching the metal of the metal tubular element comprises spraying said solution onto said tubular element. The process may be performed where the pattern of physically exposed metal comprises a pattern resulting from the combination of overlapping individual shape patterns in openings in said aperture mask and wherein each of the individual shape patterns which are used to form a developable image in said photoresist coating layer which is developed into said pattern of physically exposed metal are radiation exposed by said focussed beam of radiation through one individual shape pattern at a time.

Figure 3B:
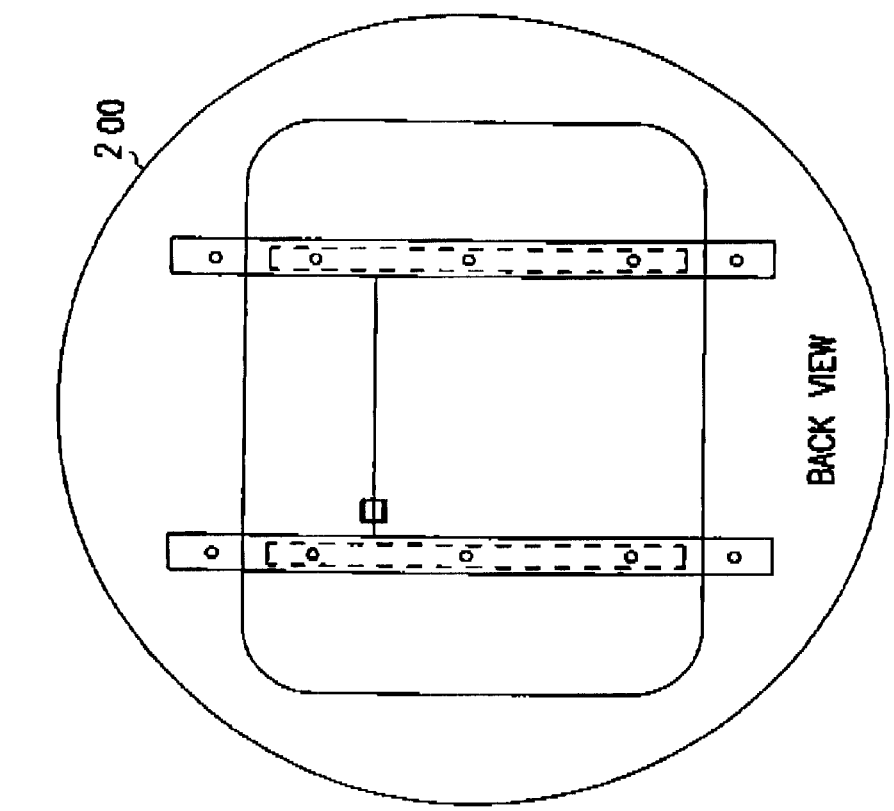
FIGS. 3(a) and (b) shows front and back views of a flat for supporting multiple cylindrical elements for etching of stents.
Figure 3A:
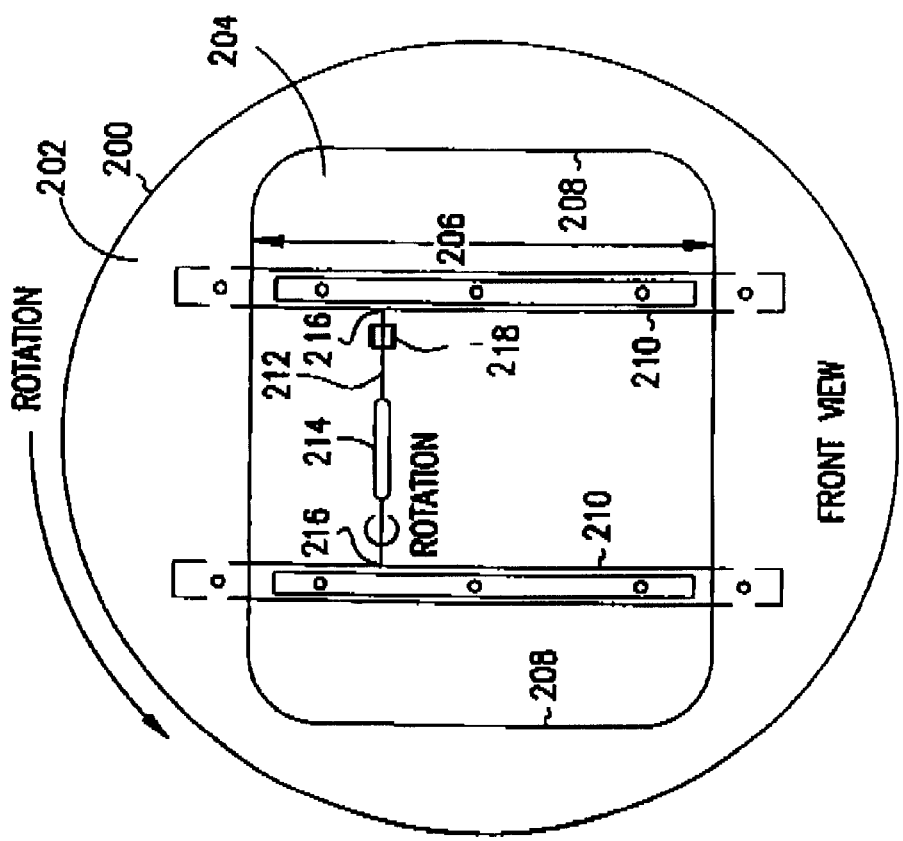

The rotating flat referred to above provides a means for supporting the cylindrical elements and for assuring their exposure to the etchant (e.g., generically a developing solution), particularly while providing a number of cylindrical elements for etching at one time. A Flat is shown in FIGS. 3(a) and (b).

The flat 200 comprises a supporting element 202 of etchant resistant material (e.g., a polymeric or composite substrate, such as polyvinyl chloride or polyolefin polymer). The supporting element 202 is a flat sheet of the polymer, cut in a generally round shape with a diameter of from 0.3 to 2.0 meters, preferably from 0.5 to 1.5 meters. There is an opening 204 in the central area of the sheet, the opening preferably having parallel sides (e.g., 206 and/or 208b) within the opening. L-bars 210 are aligned along the opposed parallel sides 206. The L-bars 210 have supports (not shown) far the support elements 212 for the cylindrical elements 214 (which may be as simple as holes (not shown) into which the ends 216 of the flexible support elements 212 may be inserted). The L-bars 210 may contain a sufficient number of opposed holes (not shown) to support the desired number (e.g., 2–3 0) of supported cylindrical elements 214 which have already had the photoresist coatings imaged, developed and otherwise prepared for the etch process. The individual support elements 212 should not overlap or be so close to each other as to prevent the ready flow of etchant between them (or be so positioned that one element might intercept sprayed etehant before its straight-line path would cause it to contact another cylindrical element.

In a preferred embodiment of the present invention, the supports for the cylindrical elements are provided in such a manner as to allow them or cause them to rotate around their longitudinal axis. In this way, the entire 360° of the surface of the cylindrical element is exposed to the spray of the etchant. The support element should therefore have a diameter of its cross section which is less than the diameter of any supporting bole (if that is the mechanism by which it is supported) on the Lbar. The support element might also be supported in a hole with bearings or other means which enables or facilitates rotation of the element. A fan-like or gear-like element or member 218 may be present on the support element (or area of the cylindrical element which is not to be etched) which will assist the etchant spray in rotating the support element (and hence rotating the cylindrical element).

In a preferred embodiment of the present invention, the supports for the cylindrical elements are provided in such a manner as to allow them or cause them to rotate around their longitudinal axis. In this way, the entire 360° of the surface of the cylindrical element is exposed to the spray of the etchant. The support element should therefore have a diameter of its cross section which is less than the diameter of any supporting hole (if that is the mechanism by which it is supported) on the L-bar. The support element might also be supported in a hole with bearings or other means which enables or facilitates rotation of the element. A fan-like or gear-like element or member 118 may be present on the support element (or area of the cylindrical element which is not to be etched) which will assist the etchant spray in rotating the support element (and hence rotating the cylindrical element).

The flat is preferably provided in a circular or ovoid shape so that it can revolve as it is rolled along its outside edge.

The Baume' of the solution is preferably higher because of the increased concentration of active etchant ingredients or standard adjuvants to etchant solutions. However, the Baume' may be increased by the addition of inert, high specific gravity or soluble materials and still provide benefits according to the present invention. There need only be at least an etchant effective amount of etchant chemistry in the solution, e.g., at least 1% by weight active etchant, preferably at least 2, 5 or 10% by weight active etchant material (e.g., at least one of active halides, oxidizing acids, oxidizing agents, chelating agents, solubilizing ingredients, etc.). The etchant solutions may comprise typical ingredients used in etch solutions such as the main chemical etching materials (e.g., metal chlorides, particularly the higher valence state metal chlorides, acids, oxidizing acids particularly, chelating agents [to maintain metal ions in solution], buffering agents, surfactants, and the like). The preferred materials are selected from aqueous solutions of ferric chloride, hydrochloric acid, hydrofluoric acid, nitric acid, sulfuric acid, organic acids (including carboxylic acids which can act as chelating agents also), metal salts (some of which are naturally formed during the etch process and remain in the solution, such as ferrous salts, nitrous salts, nitric salts, aluminum salts), phosphates, alkali metal hydroxides (to control the pH), thickening agents (e.g., silica or acrylates), and the like.

What is claimed:

1. A process for the manufacture of flexible cylindrical stents comprising:
    a) providing a hollow metal tube with an open pattern of a chemical-etch-resistant coating layer;
    b) applying a fine particulate slurry using mild agitation to said open pattern of said tube so as to ensure that each physically exposed surface of said open pattern is substantially uniform;
    c) supporting said hollow metal tube with a coating thereon on a chemical etch resistant support element;
    d) contacting the open pattern with a solution capable of etching the metal of the hollow metal tube so that said metal is etched away from physically exposed surfaces of the metal tube and openings in the metal tube corresponding to the open pattern of the coating layer are created in the metal tube element without etching said chemical etch resistant support element; and
    e) removing said metal tube from said chemical etch resistant support element.

2. The process of claim 1 wherein said contacting of the open pattern with said solution is effected by having the metal tube both rotate and revolve, and by having a spray which repeatedly alters its angle of spray towards said metal tube.

3. The process of claim 1 wherein more than one metal tube is supported on a movable support, and said movable support is passed through an area where chemical etch solution is applied by spraying.

4. The process of claim 3 wherein said spraying of said etchant solution is performed while the supported cylindrical element both rotates on a longitudinal axis and is revolved with at least some movement in a direction perpendicular to said longitudinal axis, while said solution capable of etching the metal of the metal tubular element is sprayed at a temperature between 20 and 65° C.

5. The process of claim 4 wherein said etchant solution comprises a ferric chloride solution with a Baume between 48 and 55 degrees at a temperature between 110 and 140° F.

6. The process of claim 3 wherein said etchant solution comprises a ferric chloride solution with a Baume between 48 and 55 degrees at a temperature between 110 and 140° F.

7. The process of claim 1 wherein said solution, capable of etching the metal of the hollow metal tube, contacts said metal of the hollow metal tube at a solution temperature above 40° C.

8. The process of claim 7 wherein said solution comprises ferric chloride solution with a Baume' above 47.5°.

9. The process of claim 1 wherein more than one tubular element is on the same support or said tubular element and the open pattern defines more than one tubular medical element on each tubular element.

10. The process of claim 1 wherein said open pattern is formed by wash development of a resist layer and wash development of said resist layer is performed with a developer which will develop a pattern of resist layer and contact between the resist layer and the developer is effected by spraying said developer onto a surface of said resist layer while said hollow metal tube element is rotating and with said spray being emitted from nozzles which vary their relative angle with respect to the hollow metal tube repeatedly while spraying.

* * * * *